United States Patent
Schäfer et al.

(10) Patent No.: US 12,311,407 B2
(45) Date of Patent: May 27, 2025

(54) INERTIZATION OF MATERIAL SURFACES BY FUNCTIONALIZED PERFLUORINATED MOLECULES

(71) Applicant: Technische Universität Berlin, Berline (DE)

(72) Inventors: Konstanze Schäfer, Berlin (DE); Astrid John-Müller, Berlin (DE); Stefanie Maike Krämer, Berlin (DE)

(73) Assignee: Technische Universitat Berlin, Berlin (DE)

(*) Notice: Subject to any disclaimer, the term of this patent is extended or adjusted under 35 U.S.C. 154(b) by 685 days.

(21) Appl. No.: 17/262,366

(22) PCT Filed: Jul. 30, 2019

(86) PCT No.: PCT/EP2019/070448
§ 371 (c)(1),
(2) Date: Jun. 25, 2021

(87) PCT Pub. No.: WO2020/025591
PCT Pub. Date: Feb. 6, 2020

(65) Prior Publication Data
US 2022/0176405 A1    Jun. 9, 2022

(30) Foreign Application Priority Data
Jul. 30, 2018  (EP) .................... 18186320

(51) Int. Cl.
*B05D 5/08*    (2006.01)
*B05D 3/10*    (2006.01)
(Continued)

(52) U.S. Cl.
CPC ............ *B05D 5/083* (2013.01); *B05D 3/104* (2013.01); *C03C 17/30* (2013.01); *C04B 41/009* (2013.01);
(Continued)

(58) Field of Classification Search
CPC ........ B05D 3/104; B05D 5/083; C03C 17/30; C04B 41/009; C04B 41/4556; C04B 41/466; C08J 7/126; C23C 30/005
See application file for complete search history.

(56) References Cited

U.S. PATENT DOCUMENTS

| | | |
|---|---|---|
| 2007/0172666 A1 | 7/2007 | Denes et al. |
| 2009/0043042 A1* | 2/2009 | Lippa .................. B01D 15/325 524/588 |

(Continued)

FOREIGN PATENT DOCUMENTS

WO    2007025293 A2    3/2007

OTHER PUBLICATIONS

Int'l Search Report issued for PCT/EP2019/070448, dated Dec. 16, 2019.

(Continued)

*Primary Examiner* — Nathan H Empie
(74) *Attorney, Agent, or Firm* — MaxGoLaw PLLC

(57) ABSTRACT

A method for rendering material surfaces, inert is provided. Exemplary surfaces include ceramic, metal or plastic surfaces. The method is accomplished with functionalized perfluorinated compounds for the formation of hyperhydrophobic structures on the surfaces to create inert surfaces. The inert surfaces produced or can be produced in this way have an extremely low surface energy, are resistant to deposits of substances or cells and have a very low coefficient of friction. Practical uses of the inert surfaces are also provided.

6 Claims, 1 Drawing Sheet

(51) Int. Cl.
    *C03C 17/30*     (2006.01)
    *C04B 41/00*     (2006.01)
    *C04B 41/45*     (2006.01)
    *C04B 41/46*     (2006.01)
    *C08J 7/12*     (2006.01)
    *C23C 30/00*     (2006.01)

(52) U.S. Cl.
    CPC ........ *C04B 41/4556* (2013.01); *C04B 41/466* (2013.01); *C08J 7/126* (2013.01); *C23C 30/005* (2013.01); *C08J 2375/04* (2013.01)

(56) References Cited

U.S. PATENT DOCUMENTS

| | | | |
|---|---|---|---|
| 2010/0304086 A1* | 12/2010 | Carre | G02B 27/0006 977/773 |
| 2012/0009396 A1* | 1/2012 | Sikka | C03C 17/30 427/284 |
| 2013/0280485 A1 | 10/2013 | Coclite et al. | |
| 2015/0209198 A1* | 7/2015 | Aizenberg | C09D 5/1693 428/137 |
| 2017/0043373 A1 | 2/2017 | Paxon et al. | |

OTHER PUBLICATIONS

Krajewski, et al., "Grafting of ZrO2 powder and ZrO2 membrane by fluoroalky Isilanes" Colloids and Surfaces A: Physiochemical and Engineering Aspects, Amsterdam, NL, vol. 243, No. 1-3, Jul. 17, 2004 (Jul. 17, 2004), pp. 43-47.

\* cited by examiner

INERTIZATION OF MATERIAL SURFACES BY FUNCTIONALIZED PERFLUORINATED MOLECULES

The invention preferably relates to a method for rendering material surfaces inert, preferably ceramic, metal, glass or plastic surfaces by means of functionalized perfluorinated compounds for producing hyperhydrophobic surfaces. In addition to the conventional repellent properties of fluorinated surfaces, the inert surfaces produced or can be produced in this way have additional hyperhydrophobic structures (see FIG. 1A), which increase these properties through an additional lotus effect extremely.

BACKGROUND OF THE INVENTION AND PRIOR ART

Ceramics and high-performance ceramics as well as metals usually have relatively high surface energies. Many plastics also have relatively high surface energies due to the presence of heteroatoms or functional groups. Other plastics, on the other hand, have relatively low surface energies due to their hydrophobic structure. What all these types of plastic have in common, however, is that substances or cells can usually be deposited on the surface.

Many applications in industry, in medicine or medical technology, in electrical engineering or electronics or in other areas require inert surfaces on which material accumulation is avoided or which have particularly low coefficients of friction. In these areas, plastics have become more and more important since the advancement of 3D printing, whereby the non-inert properties lead to undesirable effects.

For example, in the medical or medical technology field, a relatively high surface energy for ceramics, metals or plastics leads to the accumulation of cells. In some of these applications, for example in the field of medical implants, the accumulation of cells, in particular non-specific cell accumulation, is to be prevented.

There is therefore a great need to modify the corresponding surfaces in such a way that they are largely inert to the environment. In particular, it is desirable that the surfaces of the medical products do not interact with lipophilic or hydrophilic substances, or only interact very little, so that no cells or substances are deposited on the surface. In the case of a heart machine, for example, coagulation factors and coagulation proteins can be deposited on surfaces that are not sufficiently inert, which lead to plaque formation. The detachment of such plaques can cause heart attacks or strokes and thus represents a high medical risk.

Friction between two surfaces should often also be reduced. For biological applications in particular, WO 2012/100100A2 discloses a method in which a coating is applied to a surface which consists of a polyfluorinated or perfluorinated polymer (e.g. Teflon). This coating adheres by adhesion. In a second step, liquid perfluorocarbons (PFCs) without functional groups (i.e., PFCs that generally only consist of C and F) are applied to the first layer or hybridized. This second layer also holds itself through adhesion, since the PFCs behave very lipophilically in an aqueous environment and attach themselves to the lipophilic structures of the first layer. This creates an inert surface.

While the method described in WO 2012/100100 A2 is characterized by simple production, the PFCs only hold on to the surface through adhesion. This leads to their replacement over time. It is known that PFCs only mix with preferably the same type, different PFCs separate with one another after a certain period of time. The more similar PFCs are to one another, the longer it takes to separate. The more different the PFCs are in a mixture, the faster they separate. The interactions between the molecules of the liquid PFC layer applied are therefore greater than their interactions with the first (e.g. Teflon) layer, which is supposed to mediate between the substrate and the liquid PFCs. It is therefore to be expected that different phases will develop over time, the homogeneous liquid PFC layer being destroyed by agglomerate formation and the inert properties being impaired. The inert layers produced in WO 2012/100100A2 therefore lack a long shelf life.

Rendering plastic surfaces inert currently has a number of deficiencies in the prior art. For plastic surfaces, for example, fumigation with hydrogen fluoride (HF) is known. Rendering the surfaces inert occurs here, but it is not very effective because only individual hydrogen atoms (H) are exchanged by individual fluorine atoms (F).

The coating of plastic surfaces with polyfluorinated or perfluorinated polymers (plastics) such as Teflon is also known. In the case of poly- and perfluorinated polymers, too, only individual hydrogen atoms have been exchanged for individual fluorine atoms. Similar to the treatment with hydrogen fluoride, the perfluorinated structures achieved in this way are small and the inert properties achieved are low compared to the attachment of perfluorinated chains.

It is conceivable that perfluorinated compounds may already be incorporated during plastic production (e.g., by means of grafts or copolymers, blends, etc.), but this can lead to undesirable mechanical properties, including compromise of abrasion resistance. For example, implants with a Teflon coating had to be removed after a few years because particles rubbed off led to inflammation in the patient.

A chemical bond of perfluorinated compounds to plastic surfaces is known for the XPS (photoelectron spectroscopy) analysis method. ("Chemical derivatization for the quantification of functional groups", J. Friedrich, R. Mix, A. Meyer-Plath, S. Hanelt). Here, non-detectable functional groups of plastics are converted into a fluorine derivative in order to be able to determine the otherwise not clearly quantifiable functional groups with the aid of a fluorine concentration determination. This does not result in inertization.

Non-stick coatings with wear-resistant surfaces are also desirable in the field of tool technology for ceramic and metal surfaces, in particular with high mechanical loads, for example for preforming tools.

In the prior art it is therefore known to strive for surface modifications which are particularly inert, that is to say a low level of adhesion to the surface for foreign materials and at the same time have high abrasion resistance.

In a list by the Fraunhofer Institute for Surface Engineering and Thin Films IST in Braunschweig, commercially available coatings were identified compared to reducing surface energy:

| Coating | Surface energy [mN/m] | Hardness [GPa] | Coefficient of friction (against steel, dry) |
|---|---|---|---|
| DLC (a-C:H) | 35-40 | 20-30 | 0.10-0.20 |
| Me-DLC (a-C:H:Me) | 40-45 | 15-20 | 0.15-0.20 |
| SICAN (a-C:H:Si) | 30-35 | 10-15 | 0.07-0.15 |
| SICON ®(a-C:H:Si:O) | 22-26 | 7-9 | 0.50-0.60 |
| F-DLC (a-C:H:F) | 20-22 | 2 | — |
| CrN | 30-75 | 18-20 | 0.50-0.80 |

-continued

| Coating | Surface energy [mN/m] | Hardness [GPa] | Coefficient of friction (against steel, dry) |
|---|---|---|---|
| PTFE(Teflon ®) | 18.5 | 0.3 | 0.10 |
| Steel 100Cr6 | >1000 | 8-9 | 0.70-0.90 |

As the list shows, Teflon is characterized by a particularly low surface energy, which leads to an inert surface. However, one problem with Teflon coatings is, on the one hand, a lack of resistance to higher temperatures (above 260° C.) and, on the other hand, a lack of resistance to abrasion.

In the case of the use of Teflon for artificial acetabular sockets, abrasion resulted in the formation of particles and thus granulomas, which resulted in the prosthesis being removed. Foreign body reactions and the loosening of the implants when using Teflon-Proplast implants in the temporomandibular joint have also been described (Ga-Young Park, *Osteoblast-specific biocompatibility and mechanical properties of established and non-established polymers with regard to use as cranial implants*, dissertation Ruhr University Bochum 2012 with further references.

Because of existing disadvantages, there is a great need in the prior art to find new coatings which can be used at higher temperatures and which have high abrasion resistance.

In the case of previously known coatings that were suitable for this purpose, such as those listed in the table above, the coatings are applied to the surface by adhesion, which can reduce the abrasion resistance. Coatings that are alternative to Teflon also cannot achieve the low surface energy values of 18.5 mN/m.

The patent US 2007/0172666 A1 uses perfluorinated carbon chains $C_1$ to $C_6$ without functionalized groups for attachment. Only the plasma treatment leads to functionalized fragments of these compounds, which then react. The fragments produced in this way form randomly during the plasma treatment and thus cannot represent a homogeneous group of molecules, but this is necessary for an orderly attachment to lotus-like hyperhydrophobic structures on the material surface.

Patent WO 2007/025293 shows a process in which perfluoropropyl ether is acid-derivatized and then cross-linked on a material surface via the functional groups that are formed in the process. The acid component is then removed from the system. This creates a perfluorinated layer that only rests on the underlying material via adhesion and is not covalently bonded, which impairs the abrasion resistance. The hydrophobic properties are also reduced: the functional groups that hold the perfluorinated units are not shielded between the material surface and the perfluorinated layer, but rather bear on directly on the level of the perfluorinated layer. Therefore, there are hydrophilic interactions in these areas, which reduce the hydrophobic properties.

In the process of US000005242995A, polyurethane surfaces are activated by isocyanate groups or by an alkaline treatment. The fluorine-containing compounds preferably have hydroxyl or carbonyl groups or a halogen atom. In contrast to this, in the novel process disclosed here, polyurethane surfaces are not activated in advance, but rather subjected to perfluorination of the surface. The functionalized perfluorinated compounds used for this purpose are acid chlorides and sulfonic acid chlorides, which are inherently active enough to react with polyurethane surfaces without prior activation. The method disclosed here therefore represents a shortening and simplification of the perfluorination of polyurethane surfaces.

In the prior art, hyperhydrophobic surfaces or structures of this quality are not formed, in particular on ceramic surfaces.

OBJECT OF THE INVENTION

The object of the invention is to provide a method for rendering surfaces inert—in particular ceramic surfaces—and chemical compounds which eliminates the disadvantages of the prior art. In particular, it was the object of the invention to greatly improve the hydrophobic properties of previous fluorinated surfaces by the additional generation of hyperhydrophobic structures (see FIG. 1A). In particular, the object of the invention was to render ceramic surfaces inert, a functionalized perfluorinated compound already being provided, this functionalized perfluorinated compound comprising a perfluorinated compound and a functional group, the perfluorinated compound comprising a maximum of 20 completely fluorinated atoms. Furthermore, it is the object of the invention to ensure the abrasion resistance of the layers by means of a covalent bond and, with regard to plastic surfaces with heteroatoms (e.g., polyurethanes, polyamides, polyesters, etc.), a surface-activating pretreatment (e.g., plasma or corona treatment or acid bath) is unnecessary and thereby simplifies the process. The object of the invention is also to provide a method for rendering ceramic, metal or plastic surfaces inert as well as inerted ceramic, metal or plastic surfaces, which are characterized by a low surface energy and high abrasion resistance as well as high resistance to chemical or enzymatic degradation.

SUMMARY OF THE INVENTION

According to the present invention, the object is achieved by the independent claims. The dependent claims represent preferred embodiments of the invention.

In a preferred embodiment, the invention relates to a method for rendering material surfaces inert, comprising the following steps
  a) Provision of a material surface, in particular a ceramic surface
  b) Providing a functionalized perfluorinated compound
  c) Reaction of the functionalized perfluorinated compound with the material surface to form a covalent bond, an ionic relationship or a metal bond between the perfluorinated compound and the material surface, with preference
  d) The functionalized perfluorinated compound comprises a perfluorinated compound and a functional group, the perfluorinated compound comprising at most 20 completely fluorinated atoms.

The method according to the invention leads to the generation of a hyperhydrophobic structure, primarily through the arrangement of the functionalized perfluorinated compounds used on the material surface. Surprisingly, particularly good hyperhydrophobic surfaces or structures are obtained, in particular on ceramic surfaces when using perfluorinated compounds which comprise at most 20 completely fluorinated atoms.

In the context of the invention, the inertization of material surfaces is preferably understood to mean a modification of the surfaces which results in the modified surfaces experiencing poor adhesion or wettability by foreign materials. The described inertization of the material surfaces preferably corresponds to a reduction in the surface energy through the action of two factors: on the one hand, through perfluorination of the surface and, on the other hand, through the build-up of hyperhydrophobic structures similar to those of the lotus effect. In this way, interactions with other molecules (e.g., proteins, cells or other substances) are reduced to a minimum and highly inert hyperhydrophobic surfaces are created.

For the purpose of inertization, it is preferred that a sufficient surface density of the perfluorinated compounds is achieved so that the material surface is shielded from external molecules by the perfluorinated compounds. This is not the case when connecting perfluorinated compounds to plastics during derivatization for analytical methods.

At the molecular level, this can partly be explained by the influence of the perfluorinated compounds on electrical fields above the material surface (L. Mayrhofer J. Am. Chem. Soc., 2016, 138 (12), pp 4018-4028). A sufficient surface density of perfluorinated compounds leads to a rapid drop in the electric field above the material surface. This means that other molecules (e.g., thrombocytes [platelets] or dirt) that are trapped in the electrical field above the surface on non-perfluorinated surfaces no longer find an electric field in which they could be caught on perfluorinated surfaces. In preferred embodiments, more than 50%, preferably more than 60%, 70%, 80% or 90% of the material surface is covered by the perfluorinated compounds.

In addition, the formation of a covalent bond ensures particularly stable binding of the perfluorinated compounds, so that the inert surface properties are maintained over a long period of time.

In a preferred embodiment of the invention, the material surface is a metal, ceramic or plastic surface. However, other material surfaces, such as, for example, glass surfaces, can also be rendered inert by means of the methods described; ceramic surfaces are particularly preferred.

It is particularly preferred that the method creates a direct covalent bond between the material surface and the perfluorinated compounds. In other embodiments of the invention, however, it can also be preferred that an intermediate layer is first applied to the material surface, to which the perfluorinated compounds are covalently bound.

DETAILED DESCRIPTION OF THE INVENTION

Figures 1A, 1B:
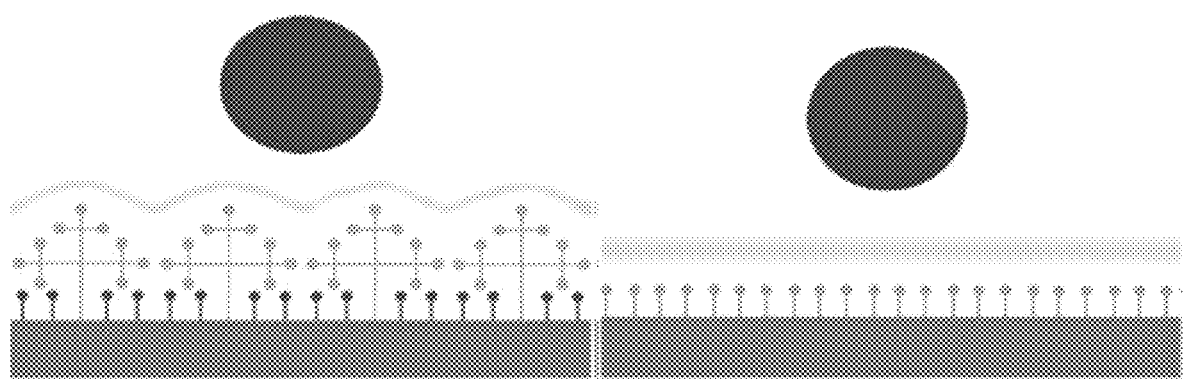
FIG. 1A depicts hyperhydrophobic surfaces are perfluorinated surfaces that have additional lotus-like structures due to the orderly attached perfluorinated molecule chains.
FIG. 1B depicts Teflon surfaces with only individual fluorine atoms pointing away from the surface.

The intended formation of a covalent bond is achieved by the functionalization of perfluorinated compounds. For the purposes of the invention, a functionalized perfluorinated compound preferably denotes a perfluorinated compound which has at least one functional group. The functional group preferably mediates the covalent bond with atoms of the material surface, preferably the ceramic, metal, plastic or glass surface or an intermediate layer. In a further connection variant between the ceramic or metal surface and the perfluorinated compounds, strong ionic relationships or metal bonds are possible.

In chemistry, covalent bonds are used to form molecules. The atomic shells of at least two atoms overlap so that the attractive electromagnetic forces between electrons and atomic nuclei come into play. In a bond, these are in equilibrium with repulsive Coulomb forces between two atomic nuclei or between electrons. If there is a difference in electronegativity (electronegativity as a measure of the ability of an atom to attract electrons) between the binding partners (up to approx. 1.5), one preferably speaks of polar bonds. With very high electronegativity differences (from approx. 1.5) the limiting case of a covalent bond comes into play, the ionic bond. This is essentially based on the electrostatic attraction between unequally charged ions.

In the case of the ceramics mentioned in the subject matter of the invention, there is often an electronegativity difference of >1.5. However, this does not have the same properties with regard to its solubility in water as is the case for substances (especially salts) with a similar difference. Salts (which are mostly present in ion lattices) such as Sodium chloride is easy to hydrate in water because the lattice energy of the ion lattice of the salt is overcome. With ceramics, this phenomenon is prevented by adapting the manufacturing process accordingly. E.g., later dissolving in water is prevented by the firing process and/or glazes. Since ceramics are rendered inert to most solvents by the manufacturing process, the application of other substances to their surface is not easily possible, which is why suitable functional groups, particularly preferably the reaction type of nucleophilic substitution, can be selected to chemically change the surface.

The functional groups of the functionalized perfluorinated compounds thus preferably allow an addition, substitution, esterification, condensation or other type of linking reactions in order to produce a covalent bond or an ionic relationship or a metal bond.

Various functionalities or functional groups with which he is able to produce covalent linkage reactions are known to the person skilled in the art.

Preferred functional groups or functionalities are selected from the group containing haloalkanes, hydroxyl, ether, amino, sulfhydryl, aldehyde, keto, carboxyl, ester and acid amide groups, groups with radicals or ions and molecules from the substance groups Carboxylic acids, peroxycarboxylic acids, thiocarboxylic acids, sulfonic acids, sulfinic acids, sulfenic acids, sulfoxides, carboxylic acid salts, sulfonic acid salts, sulfinic acid salts, sulfenic acid salts, carboxylic acid anhydrides, carboxylic acid esters, sulfonic acid esters, carboxylic acid amides, thioid amides, carboxylic acid halides, sulfonic acid amides, carboxylic acid halides, carboxylic acid amides, carboxylic acid halides, sulfonic acid amides, carboxamides, carboxylic acid halides, sulfonic acid amides, carboxylic acid halides, carboxylic acid salts, carboxylic acid halides, carboxylic acid salts, carboxylic acid halides, carboxylic acid salts, carboxylic acid halides, Alcohols, phenols, thiols, amines, imines, hydrazines, ethers, esters, thioethers, thioesters, hydrogen halides, nitro compounds, nitroso compounds, azo compounds, diazo compounds, diazonium salts, isocyanates, cyanates, isocyanides, thiocyanates, isothiocyanates, hydroperoxides, peroxides, 2'-carbamates, ethers, acid amides and thioethers or compounds that can be reactive due to their multiple bonds.

Preferred functional groups or functionalities are particularly preferred are heteroatoms such as Br, I, Cl, H, Si, N, O, S, P, hydroxyl, amino, carboxyl groups, haloalkanes, carboxamides, alcohols, hydrazines, isocyanates, thiocyanates and acid amides.

In a preferred embodiment, functionalized perfluorinated compounds are used which are suitable for nucleophilic substitution. The functional groups are preferably nucleophilic leaving groups which allow nucleophilic substitution.

In this context, nucleophilic substitution means the exchange of a group or an atom (hereinafter referred to as a leaving group) by a new group or a new atom. The leaving group should have a lower nucleophilicity than the attacking nucleophile. Here, nucleophile means a molecule that has either a negative charge (electron pair donor) or a partial charge, or which satisfies the classic concept of a Lewis base. To determine the nucleophilicity, the electronegativity and the resulting dipole or monopole are considered. The greater the electronegativity, the stronger the nucleophile.

With nucleophilic substitution, the nucleophile attacks the organic chemical molecule on the carbon atom on which the leaving group is located. Two types of reaction are used here, the first-order nucleophilic substitution (SN1) and the second-order nucleophilic substitution (SN2). These differ as follows:

Generalized Mechanism $S_N1$

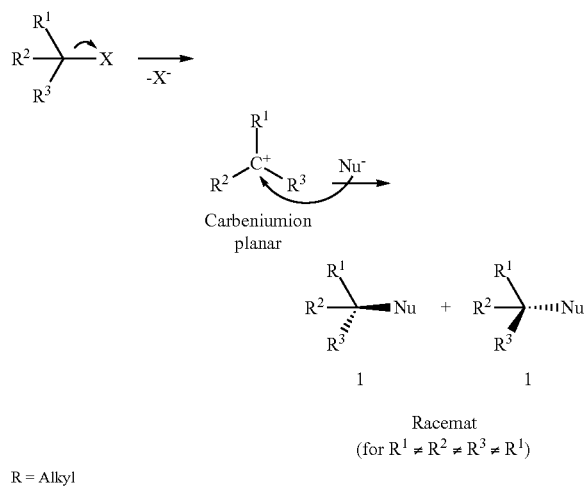

R = Alkyl
X = Leaving group

Generalized Mechanism $S_N2$

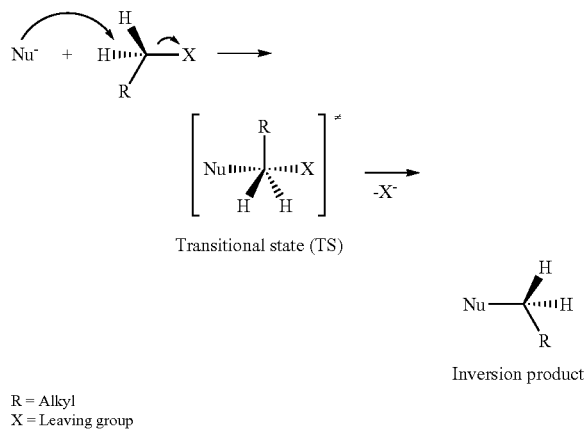

R = Alkyl
X = Leaving group

In the case of the perfluorinated hydrocarbons used here, the functional group is regarded as a nucleophile, since, as with the OH group, they are either already suitable as a nucleophile due to individual, strongly electronegative atoms, or, as in the case of the COOH group or $SO_3H$ group, can be easily deprotonated and thus receive a negative charge.

In a further embodiment, the functionalized perfluorinated compounds are bound to the surface via radical substitution, radical addition or other radical reactions.

In a further embodiment, the functionalized perfluorinated compounds are bound to the surface via UV activation or via activation using other energy sources.

In a preferred embodiment of the invention, the method is thus characterized in that the functionalized perfluorinated compounds is a perfluorinated compound with at least one functional group that comprises at least one double bond and can be attached by UV cross-linking, a perfluorinated compound with at least one functional group which can be bound to radicals or protons which are preferably formed after a plasma or corona treatment of the material surface and/or is a perfluorinated compound with at least one functional group which is suitable for the cycloaddition.

A person skilled in the art knows various forms of functional groups which are suitable for UV crosslinking, for attachment to radicals or protons, or attachment by means of cycloaddition. Various nucleophilic substitutions and suitable nucleophilic leaving groups are also known to the person skilled in the art.

In a preferred embodiment, the functionalized perfluorinated compound is a perfluorinated compound with at least one functional group, the functional group preferably being a nucleophilic leaving group, particularly preferably selected from a group comprising Br, I, Cl, H, N, O, S, P, Hydroxyl, amino, carboxyl groups, carboxylic acids, thiocarboxylic acids, sulfonic acids, sulfinic acids, carboxylic acid halides, sulfonic acid halides, acid amides, carboxylic acid amides, alcohols, sulfonic acid amides, phenols, hydrazines, thiols, amines, imines, hydrazines, isocyanates, isocyanates, With the abovementioned preferred functional groups, in particular with the preferred nucleophilic leaving groups, stable bonds are reliably and repeatably implemented. The surfaces modified in this way are also characterized by particularly high abrasion resistance.

The functionalized perfluorinated compounds preferably comprise a molecular residue consisting of a perfluorinated compound and a functionalized group for mediating a covalent bond between the perfluorinated compound and the material surface, preferably the ceramic, metal or plastic surface.

For the purposes of the invention, the perfluorinated compounds denote preferably straight or branched acyclic or cyclic, polycyclic or heterocyclic aliphatic alkanes, alkenes, alkynes, aromatic compounds or combinations of these or silanes in which all H atoms are replaced by F atoms, which are optional additionally non-fluorinated or partially fluorinated substituents with one or more functional groups or heteroatoms, in particular Br, I, Cl, H, Al, N, O, S, P, or have these in connection with one or more further functional groups.

In a preferred embodiment of the invention, the functionalized perfluorinated compounds are functionalized perfluorocarbons (PFC).

Molecules selected from the group of perfluorocarbons (PFC) denote preferably straight or branched acyclic or cyclic, polycyclic or heterocyclic aliphatic alkanes, alkenes, alkynes, aromatic compounds or combinations of these compounds in which all H atoms are replaced by F atoms are replaced, which optionally additionally at least one non-fluorinated or partially fluorinated substituent in the form of one or more functional groups, aliphatic chains or heteroatoms, in particular Br, I, Cl, H, Si, N, O, S, P, have or these are in connection with one or more further functional groups.

It is particularly preferred that the perfluorocarbons (PFC) are selected from the group containing $C_1$-$C_{100}$, preferably $C_1$-$C_{50}$, particularly preferably $C_1$-$C_{30}$, very preferably $C_1$-$C_{20}$, most preferably $C_1$-$C_{20}$ alkanes, alkenes or alkynes, the linear, branched, cyclic, polycyclic or heterocyclic, $C_6$-$C_{50}$, preferably $C_6$-$C_{30}$, particularly preferably $C_1$-$C_{20}$, aromatic or heteroaromatic systems can also be preferred. In the aforementioned compounds, the carbon atoms are preferably largely, very preferably completely, perfluorinated.

In a preferred embodiment, the functionalized perfluorocarbons comprise between 1 and 50, preferably between 1 and 20, particularly preferably between 1 and 10, very particularly preferably between 2 and 10 perfluorinated carbon atoms. The carbon atoms of the molecular residue of the perfluorocarbons, i.e., the constituent without a functional group, are preferably completely fluorinated. Typically, within the scope of the present invention, molecular residues selected from the PFC group containing —($C_nF_{(2n+2)-1}$) with n≥1, preferably n=1-20, such as —$CF_3$, —$C_2F_5$, —$C_3F_7$, —$C_4F_9$, —$C_5F_{11}$ etc., —($C_nF_{2n-1}$) with n≥2, preferably n=2-20 such as, for example —$C_2F_3$, —$C_3F_5$, —$C_4F_7$ etc., —(—$C_nF_{(2n-2)}$-1) with n≥2, preferably n=2-20, e.g., —$C_2F$, —$C_3F_3$, —$C_4F_5$, —$C_5F_7$ etc. can be used.

In a particularly preferred embodiment of the invention, the functionalized perfluorinated compound comprises a perfluorinated compound and a functional group, the perfluorinated compound comprising at most 20, very particularly preferably at most 10, completely fluorinated atoms. These preferred functionalized perfluorinated compounds lead to particularly good results (e.g., hyperhydrophobic structures, i.e., in particular hyperhydrophobic properties of the surfaces). If a solid surface is wetted with a liquid, the contact angle between the solid and liquid phase can be measured. The higher the contact angle, the more hydrophobic (water-repellent) the surface is. If the contact angle is less than 90 degrees, the material is hydrophilic, i.e., it attracts water. Such material surfaces are wetted by water. If the contact angle is between 90 and 160 degrees, one speaks of a hydrophobic material. It's water repellent; Drops of water roll off the surface, taking dirt particles with them. So the surface is washed clean by itself. However, if the contact angle is greater than 160 degrees, the material is superhydrophobic or hyperhydrophobic. If the superhydrophobic material also has a rough surface structure in the nanometer range, the water-repellent property is reinforced again. If, in a particularly preferred embodiment of the invention, the functionalized perfluorinated compound comprises a perfluorinated compound and a functional group, the perfluorinated compound comprising a maximum of 20, very particularly preferably a maximum of 10, completely fluorinated atoms, the hyperhydrophobic properties of ceramic surfaces in particular are particularly well pronounced.

Very particularly preferred perfluorinated compounds as a molecular residue are thus PFC groups with the empirical formula —($C_nF_{2n+1}$) with n 1, preferably n=1-20, preferably n=2-20, most preferably n=2-10. Further very preferred perfluorinated compounds as a molecular residue are thus groups with the sum formula $Si_nF_{2n+1}$ with n 1, preferably n=1-20, preferably n=2-20, most preferably n=2-10. These perfluorinated compounds are preferably also referred to as short-chain molecular residues.

In the prior art, it is preferred to use long-chain perfluorocarbons as macromolecules with more than 20 perfluorinated carbon atoms to render surfaces inert. The inventors have recognized, however, that in connection with functionalized perfluorocarbons which are covalently bound to the surfaces, short-chain molecules surprisingly give better results. In this way, particularly stable and long-lasting coatings can be achieved which nevertheless have excellent inert properties. In particular, by means of the aforementioned compounds, it was surprisingly possible to achieve a covalent, particularly stable inertization of material surfaces, which leads to a reduction in the surface energies to a range of 20 mN/m or less. The preferred functionalized compounds thus combine in a special way the advantageous inert properties of Teflon with high chemical and mechanical resistance Functionalized perfluorocarbons that are suitable for nucleophilic substitution are preferably used.

In a preferred embodiment of the invention, the functionalized perfluorinated molecules are based on one of the following substances:

F($CF_2$)nX, where n=1-50, preferably n=1-10, and X=Br, I, Cl, H or X=Si, N, O, S, P, in connection with a functional group, especially $C_8F_{17}I$, $C_8F_{17}Br$;

F($CF_2$)$_n$—($CH_2$)$_m$X, where n=1-50, preferably n=1-10, m=1-26, preferably m=1-6 and X=Si, N, O, S, P, Br, I, H;

F($CF_2$)$_n$—$O_b$—CH=$CH_2$ with n=1-50, preferably n=1-10, and b=0 or 1, preferably b=0;

$C_6F_{13}CH_2CH_2MgI$, ($C_6F_{13}CH_2CH_2$)$_3$SnPh, ($C_6F_{13}CH_2CH_2$)$_3$SnBr, ($C_6F_{13}CH_2CH_2$)$_3$SnH;

$C_2F_5I$, $C_3F_7Br$, $C_4F_9I$, $C_5F_{11}Br$, $C_6F_{13}Br$, $C_8F_{15}Br$, $C_{10}F_{17}I$, $C_4F_9CH=CHC_4F_9$, $C_8F_{16}Cl_2$, $C_{10}F_{19}N$, $C_6F_{19}Br$, $C_9F_{21}N$, $C_{10}F_{21}Br$, $C_{11}F_{22}N_2O_2$, $C_6F_{13}CH=CHC_6F_{13}$, $C_{12}F_{27}N$, $C_{16}F_{25}Br$;

$C_8F_{17}I$, $C_8F_{17}Br$

Organometallic organyls (e.g., organyl lithium) are also particularly preferred as functionalized perfluorinated molecules, i.e., perfluorinated carbon atom compounds, with a metal attached to at least one carbon atom.

The preferred modifications lead to surfaces with extremely low surface energies and the properties resulting therefrom such as chemical resistance, very low surface friction, prevention of the accumulation of hydrophilic or lipophilic substances or of cells.

Furthermore, the modifications are resistant to enzymatic degradation (for example by hydrolases or proteases), which makes them particularly suitable for medical applications. In addition, the modifications are biocompatible and can be used medically, since similar molecules are already used in medical applications for other functions, for example as contrast media or as blood substitutes.

Further preferred starting substances of the functionalized perfluorinated compounds from the group of PFCs which can be used in the context of the invention are:

perfluorinated cholesteryl and adamantyl compounds, perfluorinated cis-eicosenoic, perfluorinated aromatic compounds, perfluorinated pyrenes, perfluorinated glycerides; and

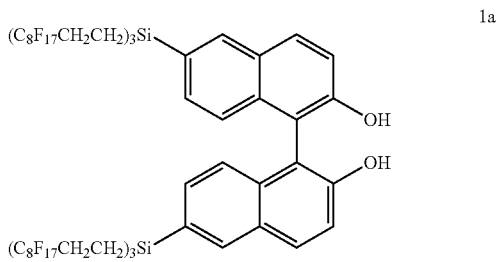

1a

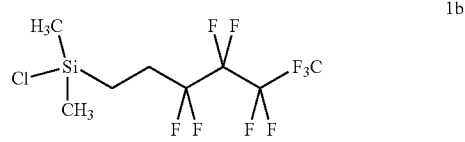

1b

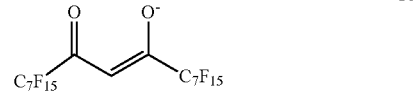

1c

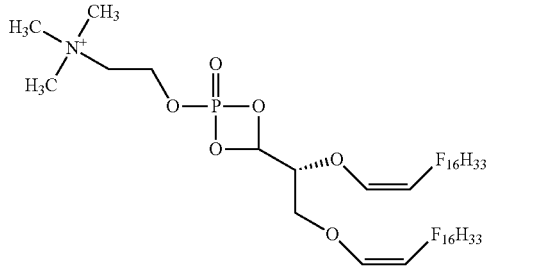

1d

1e
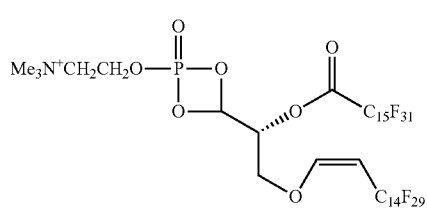
1f
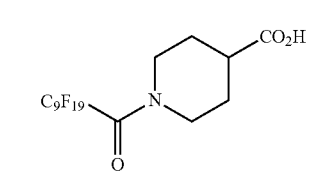
1g
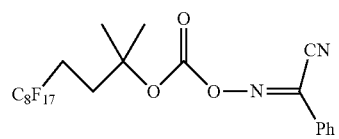
1h
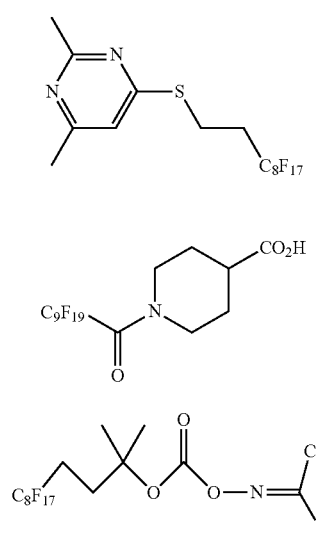
1i
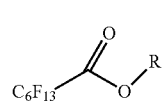
1j
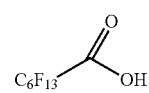
1k
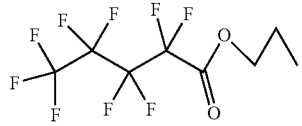
1l
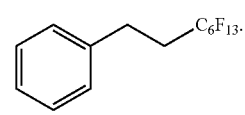
for linking in the form of an ionic bond, e.g., the following PFCs are used:
1m
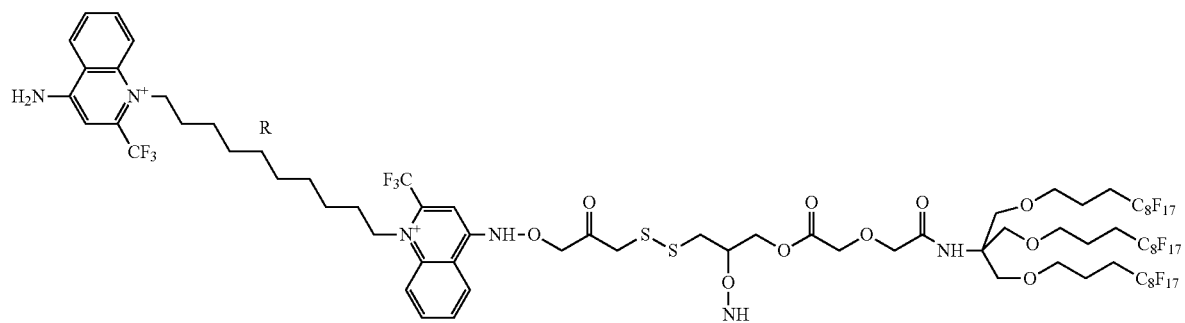
R = Perfluoro moiety
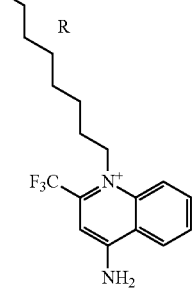

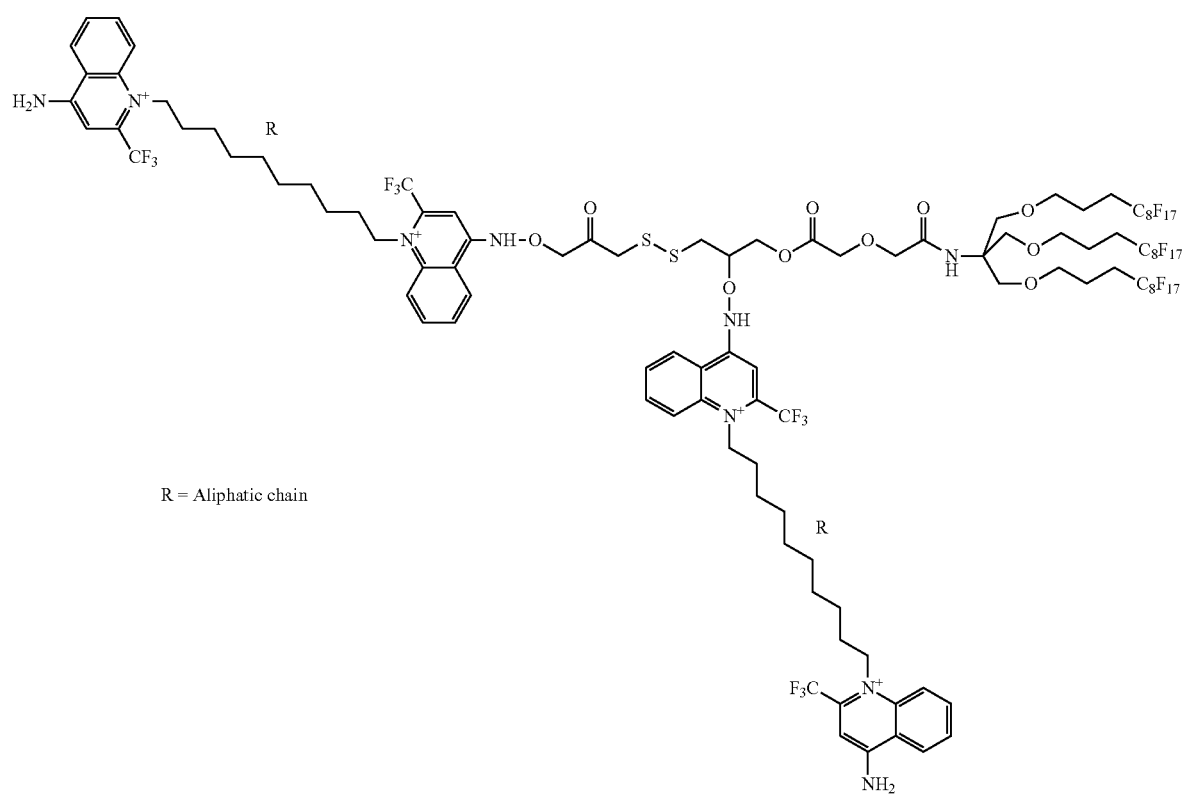
R = Aliphatic chain
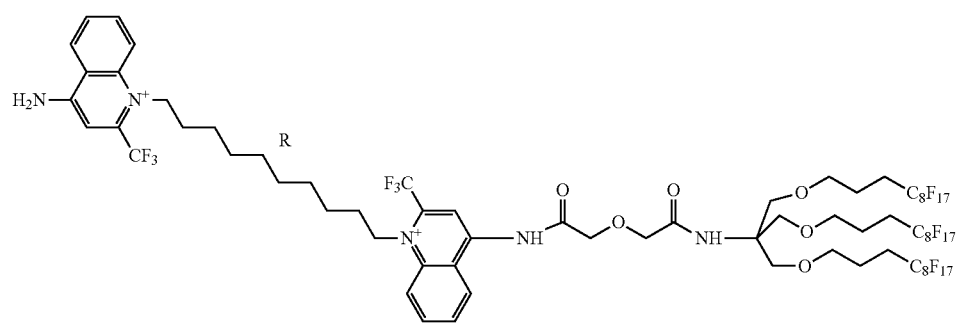
with R=perfluorocarbon radical or aliphatic chain;

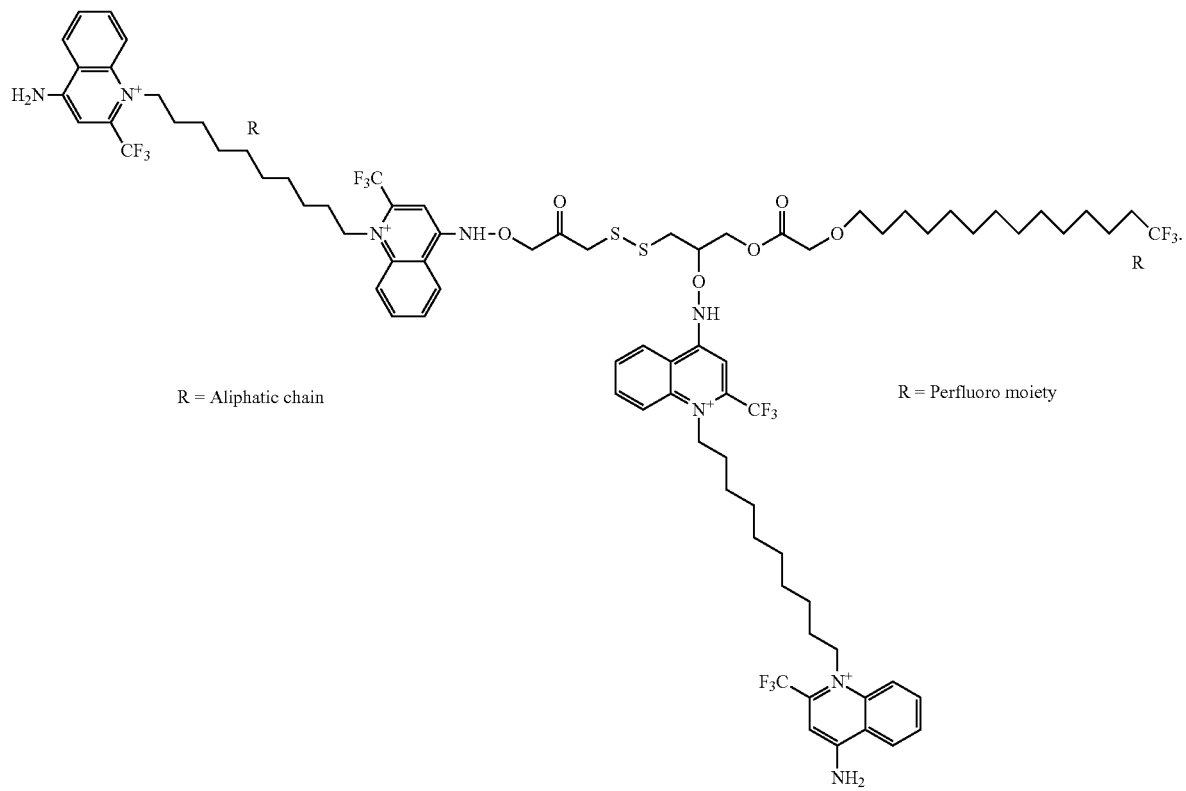

In a preferred embodiment of the invention, the perfluorinated compounds are perfluorosilicon compounds.

In this embodiment, the perfluorinated part or molecular residue (moiety) comes from the group of perfluorosilicon compounds containing straight or branched acyclic or cyclic, polycyclic or heterocyclic aliphatic silanes in which all H atoms are replaced by F atoms, the optionally also non-fluorinated or partially fluorinated substituents with one or more functional groups or heteroatoms, in particular Br, I, Cl, H, Al, N, O, S, P or have these in connection with one or more further functional groups.

Perfluorosilicon compounds from the group containing Si1-Si100, preferably Si1-Si50, particularly preferably Si1-Si30, very preferably Si1-Si20, most preferably Si1-Si20 perfluorinated silicon compounds are used. As in the case of the PFCs, the perfluorosilicon compounds are also functionalized with suitable substituents. I.e., the functionalized perfluorosilicon compounds have a perfluorinated part or molecular residue (moiety), as described above, and additionally at least one functional group for mediating a covalent bond.

In a preferred embodiment, the functionalized perfluorosilicon compounds comprise between 1 and 50, preferably between 1 and 20, particularly preferably between 1 and 10, very particularly preferably 2 and 10 perfluorinated Si atoms. The Si atoms of the remainder of the molecule, i.e., the constituent without a functional group, are preferably completely fluorinated.

Perfluorosilicon compounds from the group comprising Si1-Si100, preferably Si1-Si50, particularly preferably Si1-Si30, very preferably Si1-Si20, most preferably Si1-Si20 perfluorinated silicon compounds are used. As in the case of the PFCs, the perfluorosilicon compounds have suitable substituents. Further preferred functionalized perfluorosilicon compounds can be selected from the following group:

Siloxanes of the general formula —[—$SiR_2$—O—]$_n$— with n≥1 and R=perfluorinated carbon or F, Siloxanols of the general formula HO-A-[—$SiR_3R_4$—O—]—$SiR3R4R5$ with R3, 4, 5=F or —$F(CF_2)_n$, with n=1-10 and A=alkyl chain Perfluorinated silicates, silicic acids, sodium silicates, polysilazanes, silicides, silicon tetrahalides, silicones, silicone oils, zeolites, zirconium silicates.

Silanes of the general formula X—$CH_2$—$Si(OR)_3$, where X is a leaving group suitable for nucleophilic substitution with X=Cl, Br, I, H, OH or functional groups comprising amino, vinyl, carbamato, glycidoxy-, methylalkoxy, phenyl or acetoxy groups and R=F or —$F(CF_2)n$ with n=1-10, Silanes of the general formula X—$Si(CF_3)_3$ or X—$Si(R)_3$, where X is a leaving group suitable for nucleophilic substitution with X=Cl, Br, I, H, OH or functional groups such as amino, vinyl-, carbamato, glycidoxy, methylalkoxy, phenyl or acetoxy groups and R=F or R=$F(CF_2)_n$ with n=1-10.

In a further embodiment, the perfluorinated compound is selected from the group of further perfluorinated compounds, wherein it is based on compounds selected from $NF_3$, $N_2F_4$, $SNF_3$, $CF_3SN$, $SF_4$, $SF_6$, perfluorinated nitrogen-sulfur compounds.

In a further embodiment, the perfluorinated part of the molecule consists of fluorine-phosphorus compounds or fluorine-aluminum compounds.

In these cases too, it is particularly preferred for the perfluorinated compound to be characterized by short-chain molecules.

In a preferred embodiment, the functionalized perfluorinated compounds comprise between 1 and 50, preferably between 1 and 20, particularly preferably between 1 and 10, very particularly preferably 2 and 10 perfluorinated atoms, the atoms preferably also being selected from the group C, Si, S or N or combinations of these such as, for example, SN (nitrogen-sulfur).

The atoms of the constituent of the perfluorinated compound with no functionality are preferably completely fluorinated. I.e., all hydrogen bonds to the atoms have been substituted by fluorine.

It can also be preferred that the perfluorinated compound contain two or more perfluorinated molecules selected from the group of perfluorocarbons (PFC), perfluorosilicon compounds and other perfluorinated compounds.

Typically, the functionalized perfluorinated compounds described above can be combined into several units. The following molecules are examples:

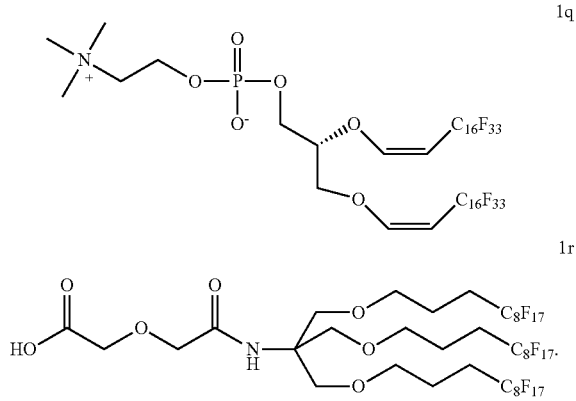

The attachment of these molecules to the other molecules contained in the compound according to the invention can take place via $NH_2$ groups or OH groups or other suitable groups.

A large number of different ceramic surfaces can advantageously be rendered inert by the functionalized perfluorinated compounds disclosed.

In the context of the invention, the term ceramic includes ceramic materials that are inorganic, non-metallic and polycrystalline.

The ceramic can be selected, for example, from a group containing aluminum oxide, zirconium oxide, aluminum titanate, silicon carbide, silicon nitride or aluminum nitride or other non-metallic or metallic substances or dispersion ceramics and piezoceramics, porcelain, stoneware, stealite, glass ceramic, cordlerite, titanium oxide, yttrium oxide, beryllium oxide, magnesium oxide, uranium oxide, titanates, lead titanium zirconate, ferrites, carbon, nitrides, carbides, borides, silicides (silicon, boron, titanium, molybdenum).

High-performance ceramics or technical ceramics that have been optimized for technical applications are particularly preferred. For example, these can have special hardnesses, conductivities or temperature behavior, etc. in order to meet the respective requirements for the desired application.

Materials for high-performance ceramics such as made of aluminum oxide, zirconium oxide, aluminum titanate, silicon carbide, silicon nitride or aluminum nitride or other non-metallic or metallic substances or dispersion ceramics and piezoceramics have become more and more important since the advancement of 3D printing. They are used in a growing number of areas, including in the medical field (implants, dental technology) and in areas of high mechanical stress and in substrates stabilized in zirconium oxide. The property of some of these substances to be particularly conductive or magnetic or diamagnetic, hide other interesting areas of application.

In a preferred embodiment of the invention, the ceramic surface is formed by a ceramic which is selected from a group containing aluminum oxide, zirconium oxide, aluminum titanate, silicon carbide, silicon nitride or aluminum nitride or other non-metallic or metallic substances or dispersion ceramics and piezoceramics, porcelain, stoneware, stealite, glass ceramics, cordlerite, titanium oxide, yttrium oxide, beryllium oxide, magnesium oxide, uranium oxide, titanates. Lead titanium zirconate, ferrites, carbon, nitrides, carbides, borides, silicides (silicon, boron, titanium, molybdenum), with high-performance ceramics in particular aluminum oxide, zirconium oxide, titanium oxide, aluminum titanate, silicon carbide, silicon nitride or aluminum nitride being particularly preferred.

Excellent results were achieved in particular for the last-mentioned high-performance ceramics, very preferably aluminum oxide, zirconium oxide, titanium oxide, aluminum titanate, silicon carbide, silicon nitride or aluminum nitride. Not only can the functionalized perfluorinated compounds be covalently bonded to them in a simple manner and stabilized, but the compounds also achieve particularly homogeneous coverage and inertization. Surprisingly, the functionalized perfluorinated compounds, especially in the case of short-chain perfluorinated molecular residues, receive the other advantageous properties that characterize high-performance ceramics, such as e.g., Hardness, corrosion resistance, abrasion and wear resistance, etc.

Exemplary preferred ceramic compounds include i.a. following particles MgO, $ZrO_2$, $B_4C$, $S_3C$, $Si_3N_4$, BN, $Al_2TiO_5$, $Pb(Zr,Ti)O_2$, $BaTiO_3$, AlN or $Al_2O_3$.

Advantageously, the functionalized perfluorinated compounds disclosed can also be used to render various metal surfaces inert.

In a preferred embodiment, the metal surface is formed by a metal selected from a group containing titanium, aluminum, cadmium, chromium, iron, gold, iridium, cobalt, copper, nickel, palladium, platinum, silver, zinc and tin and alloys that contain these contain such as titanium alloys or stainless steel, very particularly preferably the metal surface is formed from titanium or a titanium alloy.

The metals mentioned as preferred, in particular titanium, can be successfully coated with the functionalized perfluorinated compounds in a similar way as for the ceramics.

Due to the inertization by means of the functionalized perfluorinated compounds described, the metals can be used in a variety of ways. Especially for medical applications e.g., for implants with metal components, the covalent attachment of the functionalized perfluorinated compounds can ensure that there is no unwanted accumulation of biological material or cells.

In a preferred embodiment, the plastic surface is formed from a plastic selected from a group comprising polyacetals, polyacrylates, polyamides, polyaryls, celluloses, polyesters, polyolefins, polystyrenes, polyvinyacatates, polyvinyl chlorides, polyether ketones, polyaryl ether ketones, polylactides, amino resins, epoxy resins, polyether alcohols, Fluorocarbon elastomers, ester elastomers, isoprene elastomers, olefin elastomers, silicone elastomers, pentenes elastomers, sulfide elastomers, urethane elastomers and vinyl chloride elastomers. For the aforementioned plastics, functionalized perfluorinated compounds can be stably bound in a simple manner using the processes described. The inertized plastic surfaces obtained in this way can be used in a variety of ways and are used, for example, in medical products, but also in everyday products, effectively preventing the build-up of biological material or dirt particles.

The inertization according to the invention by means of the functional perfluorinated compounds described can be implemented in various ways.

On the one hand, the ceramic or metal surfaces can be preactivated by acids (e.g., with sulfuric acid or hydrofluoric acid), by other agents, by laser treatment, by corona or plasma treatment, by ozone treatment or other processes and subsequent reaction with functionalized perfluorinated compounds for covalent bonding or lead to an ionic relationship or a metal bond. A direct reaction with functionalized perfluorinated compounds without preactivation can also be provided. Furthermore, it can also be preferred that the ceramic or metal surfaces are coated with an intermediate layer with which the functionalized perfluorinated compounds react.

In a preferred embodiment of the method, the material surface is activated before the reaction of the functionalized perfluorinated compounds, the activation preferably taking place by acid, laser, corona, ozone or plasma treatment.

This embodiment is particularly preferred in connection with functionalized perfluorinated compounds which have nucleophilic leaving groups as functional groups.

The activation of the material surface, preferably the ceramic, metal or plastic surface, preferably leads to the fact that it becomes electrophilic or forms electrophilic groups. A nucleophilic substitution using the preferred functionalized perfluorinated compounds attacks the electrophilic groups and leads to a covalent bond.

Various methods for activating a surface are known to the person skilled in the art.

For example, it may be preferred to use acids for this purpose, particularly preferably a hydrogen fluoride (hydrofluoric acid) or a sulfuric acid. However, other activations, for example by means of plasma or laser irradiation, are also conceivable.

In a preferred embodiment of the invention, different activation takes place for partial areas of the material surface. In this way, different degrees of inertization can be implemented on the material surface in a controlled manner. For example, it may be preferred to activate certain sub-areas while other sub-areas are not activated, so that the perfluorinated compounds only bind to the activated sub-areas. Intermediate stages of differently graded activation in order to produce coatings with different densities of the perfluorinated compounds can also be provided.

Such a selective surface treatment, i.e., a different activation of the sub-areas e.g., A defined pattern between areas of different properties (e.g., high and very low surface energy) can advantageously be generated by laser treatment or by a selectively generated print image and the associated accessibility or non-accessibility for the reactions with the functionalized perfluorinated compounds.

In a preferred embodiment of the invention, different activation takes place for partial areas of the material surfaces according to a predetermined pattern, so that a different inertization of the ceramic or metal surface is implemented according to the predetermined pattern.

For example, areas of strong surface energy (large interactions with the environment) and areas of very low surface energy (low interactions with the environment) can be generated selectively under physiological conditions. Or the friction between two sub-areas of surfaces can be reduced in a targeted manner.

In a further preferred embodiment, the invention relates to ceramic or metal surfaces rendered inert, the perfluorinated compounds being covalently bonded to a ceramic or metal surface.

In a preferred embodiment, the invention relates to inertized material surfaces, preferably ceramic, metal or plastic surfaces that can be produced or produced by a method according to the invention or preferred embodiments thereof, so that the perfluorinated compounds are covalently bonded to a material surface, preferably a ceramic, metal or plastic surface.

Inertized material surfaces, preferably inertized ceramic, metal or plastic surfaces, in the context of the invention preferably means a material surface which, as a result of inertization, has low adhesion or wettability by foreign materials. The inertized material surface, preferably the inertized ceramic, metal or plastic surface can also be referred to as an inert ceramic, metal or plastic surface.

The inertized material surfaces are characterized by the advantages described. In particular, the inertized material surfaces are characterized by extremely low surface energies, as a result of which they have a high chemical resistance, low surface friction and a reduced ability to adhere to foreign materials. In particular, an accumulation of hydrophilic, lipophilic substances or cells is effectively prevented on the material surfaces according to the invention which have been rendered inert, so that they are particularly suitable for medical applications.

The person skilled in the art recognizes that preferred embodiments and advantages which are described for the method for inertizing material surfaces also apply to the inertized material surfaces. For example, it was disclosed for the method that functionalized PFCs are preferably used. The person skilled in the art recognizes that, in a preferred embodiment, the material surfaces rendered inert are characterized by a covalent bond of PFCs, as perfluorinated compounds.

In preferred embodiments, in the case of the inertized material surfaces, preferably the ceramic, metal or plastic surfaces, the perfluorinated compounds can be connected to the surface of the material, preferably the metal, the ceramic or the plastic, for example from a group, by a linker or spacer molecule Containing in particular haloalkanes, hydroxyl, ether, amino, sulhydryl, aldehyde, keto, carboxyl, ester and acid amide groups, groups with radicals or ions and molecules from the substance groups of carboxylic acids, peroxycarboxylic acids, thiocarboxylic acids, sulfonic acids, sulfinic acids, sulfenic acids, sulphoxides, carboxylic acid salts, sulphonic acid salts, sulphinic acid salts, sulfenic acid salts, carboxylic acid anhydrides, carboxylic acid esters, sulfonic acid esters, carboxylic acid halides, sulfonic acid halides, carboxamides, sulfonic acid amides, carboxylic acid hydrazides, ketaldehyde, ketaldehyde, ketaldehyde, ketaldehyde, phenyl alcohol, ketaldehyde, phenyl alcohol, hiols, amines, imines, hydrazines, ethers, esters, thioethers, thioesters, hydrogen halides, nitro compounds, nitroso compounds, azo compounds, diazo compounds, diazonium salts, isocyanates, cyanates, isocyanides, thiocyanates, isothiocyanates, hydroperoxides, peroxides or compounds that are reactive due to their multiple bonds can, or functionalized perfluorocarbons with iodine, bromine or sulfur atoms, carbamates, thioether or disulfide groups, glycerol, succinylglycerol, phosphate groups and functionalized perluorocarbons with other groups or atoms, via which a connection to nucleosides, nucleotides, oligonucleotides, modified nucleic acids, modified nucleotides, modified oligonucleotides, modified nucleic acids, peptide nucleosides, peptide nucleotides, peptide oligonucleotides, peptide nucleic acids or pharmaceutical substances can be produced.

In preferred embodiments, in the case of the inertized material surfaces, preferably the ceramic, metal or plastic surfaces, the perfluorinated compounds can be connected to the surface of the material, preferably the metal, the ceramic or the plastic, for example from a group, by a linker or spacer molecule Containing in particular haloalkanes, hydroxyl, ether, amino, sulhydryl, aldehyde, keto, carboxyl, ester and acid amide groups, groups with radicals or ions and molecules from the substance groups of carboxylic acids, peroxycarboxylic acids, thiocarboxylic acids, sulfonic acids, sulfinic acids, sulfenic acids, sulfoxides, carboxylic acid salts, sulfonic acid salts, sulfinic acid salts, sulfenic acid salts, carboxylic acid anhydrides, carboxylic acid esters, sulfonic acid esters, carboxylic acid halides, Preferred linker molecules are based on hydroxyl or amino groups, carboxyl groups, polyamides, ethers, thioethers, thioesters, carboxylic acids, Carbamates, disulfide bridges and hydrazides, haloalkanes, sulhydryl, aldehyde, keto, carboxyl, ester and acid amide groups, thiols, amines, imines, hydrazines, or disulfide groups, glycerol, succinylglycerol, orthoesters, phosphoric acid diesters and vinyl ethers, with ester and Ether groups and disulfide bridges are very particularly preferred.

In a preferred embodiment, the material surface rendered inert is characterized in that the covalent bond takes place through a linker or spacer molecule, the linker or spacer molecule preferably being based on hydroxyl or amino groups, carboxyl groups, esters, ethers, thioethers, thioesters, carboxamides, compounds with Multiple bonds, carbamates, disulfide bridges and hydrazides, haloalkanes, sulhydryl, aldehyde, keto, carboxyl, ester and acid amide groups, thiols, amines, imines, hydrazines or disulfide groups, glycerol, succinylglycerol, orthoesters, phosphoric acid diesters and vinyl ethers—and ether groups and disulfide bridges are very particularly preferred.

The linker molecule can advantageously be used to connect further functional molecules which, for example, generate electrical conductivity or which force the growth of cells. Other examples are the connection of growth factors or the connection of molecules that have functions that differ from the properties of the environment.

Examples of such suitable molecules would be molecules in the field of molecular electronics or sensor technology (ferroceene compounds and others), growth factors such as fibroblast growth factor (FGF), vascular endothelial growth factor (VEGF), nerve growth factor (nerve growth factor, NGF), metallic conductive compounds or molecules biocompatible interfaces between inorganic and organic materials.

In a further preferred embodiment, the invention relates to the use of a material surface rendered inert with the described method, preferably a ceramic, metal or plastic surface in a medical product, preferably in an implant in which cell attachment is preferably wholly or partially undesirable, particularly preferably in one heart implant, a stent, a prosthesis, a joint, in dental implants or in medical technology equipment through which substances, in particular blood or blood components, are passed.

Medical products in which the inertized material surfaces, preferably the ceramic, metal or plastic surfaces are used, are advantageously distinguished by a particularly high biocompatibility and have an extremely low risk of complications.

In the context of the invention, an implant preferably denotes a medical device to replace, support or improve a biological structure. A dental implant preferably denotes an implant for the mouth or jaw area and can preferably both replace and support tooth structures. A heart implant is preferably understood to mean a device which simulates the function of the human heart, for example to bridge the time a patient has to wait for a donor heart.

Due to the inert properties of the ceramic or metal surfaces, the medical products are characterized by particularly low deposits and can therefore be worn in the body for long periods of time without deposits or wear leading to complications.

In a further preferred embodiment, the invention relates to the use of the inertized material surfaces, preferably the ceramic or metal surfaces, in a product of electrical engineering, in particular of microelectronics. In electrical engineering and microelectronics, high-performance ceramics and metals are used in a variety of ways as materials for increasingly complex components. Due to static charges, material or dust deposits often occur, which even as microdeposits can reduce the performance and service life of the devices. This can be effectively avoided with the ceramic or metal surfaces made inert according to the invention. Advantageously, the described methods, in particular using short-chain perfluorinated compounds, also ensure that the desired electrical properties of the ceramic or metal surfaces are not changed by the inertization. It is known that the electrical field of a material above perfluorinated interfaces is comparatively very small. Electrostatic attraction cannot develop as a result.

In a further preferred embodiment, the invention relates to the use of the inertized material surfaces in window glasses, furnishings, sanitary installations or buildings. The described method can advantageously also be used for inerting glass surfaces or ceramics, which are typically used in window glass, furnishings, sanitary installations or buildings. In the aforementioned applications, material surfaces rendered inert in this way are characterized by the fact that no or only little dirt can accumulate on them. This can significantly reduce the cleaning effort.

The invention is to be explained in more detail below using examples, without being restricted to these.

Explanation for FIG. 1A: Hyperhydrophobic surfaces are perfluorinated surfaces that have additional lotus-like structures due to the orderly attached perfluorinated molecule chains. In contrast to Teflon surfaces (FIG. 1B) with only individual fluorine atoms pointing away from the surface, the effectiveness of hyperhydrophobic surfaces is extremely increased. Perfluorinated surfaces with attached irregular perfluorinated chains are not able to build up ordered hyperhydrophobic structures.

It is pointed out that various alternatives to the described embodiments of the invention can be used in order to carry out the invention and to arrive at the solution according to the invention. The methods according to the invention and inerted ceramic and metal surfaces are therefore not limited in their explanations to the preferred embodiments mentioned. Rather, a large number of design variants are conceivable, which can differ from the solution shown. The aim of the claims is to define the scope of the invention. The scope of protection of the claims is aimed at covering the methods according to the invention and inertized material surfaces, preferably the ceramic, metal and plastic surfaces and equivalent embodiments of these. The parts by weight of the components are sometimes given with the abbreviation "parts".

Examples of Ways of Inerting Ceramic and Metal Surfaces with Functionalized Perfluorinated Compounds:

Modifications of ceramic and metal surfaces with functionalized perfluorinated compounds can be implemented in various ways:
1) Pre-activation of the surfaces by acids (e.g., with sulfuric acid or hydrofluoric acid), by other agents, by laser treatment, by corona, ozone or plasma treatment or other processes and subsequent reaction with functionalized perfluorinated compounds
2) direct reaction with functionalized perfluorinated compounds
3) Coating with a layer on which functionalized perfluorinated compounds can react By means of a selective surface treatment (e.g., laser treatment) or a selectively generated print image and the associated accessibility or non-accessibility for the reactions with the functionalized perfluorinated compounds, a defined pattern between areas of different properties (e.g., high and very low surface energy) can be created.

Regarding 1) and 2) (Pre) Activation of the Surfaces with Sulfuric Acid or Hydrofluoric Acid and Subsequent Reaction with a Functionalized Perfluorinated Compound or Direct Reaction:

Based on the depicted unit cell of the crystalline structure of zirconium (IV) oxide, various modification processes are possible, with several reactions for changing the surface structure being available as options.

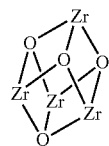

Since high-performance ceramics made from zirconium (IV) oxide and others have a high chemical and thermal stability, it may be preferable to carry out surface activation using hydrofluoric acid (hydrofluoric acid) and/or concentrated sulfuric acid. In some cases, however, it can be dispensed with (direct reaction).

As a result of the activation, the oxygen atoms aligned with the surface are first protonated. If another protonation takes place, the oxygen atoms can be split off as water (see reaction equation 1).

Reaction equation 1: Protonation of the oxygen atoms of $ZrO_2$

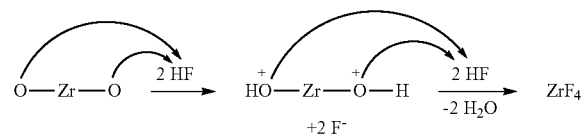

By splitting off the oxygen, the zirconium atom can exist as a tetravalent ion ($Zr^{4+}$) and form an ionic compound with the fluoride ions (salt). This detaches the zirconium ion from the surface structure of the ceramic and is "rinsed out".

In this way, different activated states of the $ZrO_2$ surface structure can be generated in one pretreatment. These are the starting point for the modification with functionalized perfluorinated compounds.

Reaction equation 2: nucleophilic substitution on the activated ceramic surface

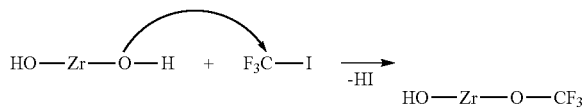

As reaction equation 2 shows, the activated first protonated state of the ceramic can nucleophilically attack the positively charged perfluorinated methyl iodide carbon, so that a perfluorinated methyl group is added. The perfluorinated "ether" formed is more difficult for body cells to split than a non-perfluorinated methyl group, since the fluorine atoms contained in it represent poor leaving groups due to their low relative atomic mass, high electronegativity and their small radius (ionic radius) and are therefore not split off.

In addition, methyl groups with their hydrogen atoms can form both van der Waals interactions and hydrogen bonds, which is clearly more difficult with the perfluorinated radicals.

This makes it possible to use other perfluorinated groups for modification, which bind to the activated ceramic surface by means of basic reaction mechanisms.

Reaction equation 3: activated ceramic surface as electrophile

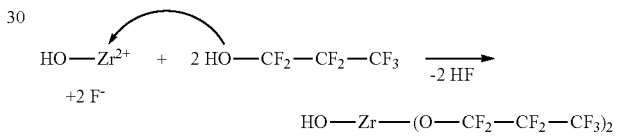

As reaction equation 3 shows, the ionic activated intermediate can also be used as an electrophilic reactant. The zirconium ion is attacked nucleophilically by the perfluorinated alcohol. The perfluorinated "diether" is formed by splitting off hydrofluoric acid (which can re-enter the reaction process for further surface activation).

Reaction equation 4: activated ceramic surface as electrophile

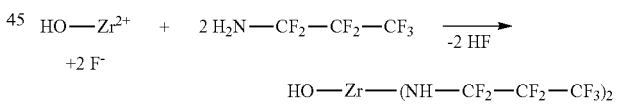

Analogously to reaction equation 3, reaction equation 4 also shows a possible reaction in which the activated ceramic surface is used as an electrophilic reactant. A primary amine is used as the nucleophilic reaction partner. Perfluorinated secondary amines can also fulfill this type of reaction. The amine attacks the positively charged zirconium by means of the lone pair of electrons in nitrogen and binds to it. A proton (H+) is split off and forms HF with the fluoride ion, which is available again for surface activation.

Reaction equation 5: Attachment of a perfluorinated silane to the activated ceramic surface

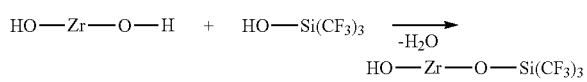

Based on "silicones", perfluorinated silanes can be used. This type of reaction corresponds to a condensation in which water is split off as a by-product (see reaction equations 5 & 6). The silane oxygen nucleophilically attacks the positively polarized zirconium. One H⁺ and one OH⁻ group are split off as water.

Reaction equation 6: Attachment of a perfluorinated silane to the activated ceramic surface

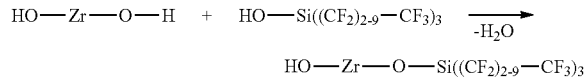

As in reaction equation 5, the silane oxygen nucleophilically attacks the zirconium and an H⁺ and an OH group are split off as OH⁻, which form the by-product water.

The introduction of silanes or other semimetals or metals (doping) is used to increase the electrical conductivity. Zirconium (IV) oxide can electrolytically transport oxygen ions at high temperatures. This creates an electrical voltage. The doping improves the conductivity at lower temperatures.

In contrast, the application of perfluorinated organyls to the zirconium (IV) oxide surface reduces or prevents the conduction of electrical current. In electrical engineering (microelectronics), this isolator effect enables precise production of control systems for conducting electrical current.

Reaction equation 7: addition and hydrogenation of tetrafluoroethene on the activated ceramic surface $$HO-Zr^{2+} + 2H_2 + 2CF_2=CF_2 \longrightarrow HO-Zr(CF_2H-CF_2H)_2$$

By means of the double bond of the tetrafluoroethene, an addition takes place on the electrophilic zirconium. Subsequent hydrogenation (addition of H2) reduces the former ethene group.

Reaction equation 7 shows an analogue to the first step of the Ziegler direct method. The tetrafluoroethene is additively attached to the activated zirconium oxide surface and hydrogenated.

Rection equation 8: reaction of a perfluorinated metal organyl with the activated cermaic surface

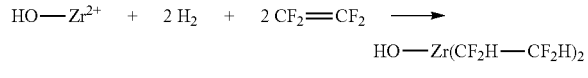

Reaction equation 8 shows the reaction of a perfluorinated metal organyl (lithium organyl, a copper-lithium organyl would also be possible, for example). The perfluorinated organyl is a strong nucleophile that nucleophilically attacks the positive zirconium ion on the activated ceramic surface. This reaction is also promoted by the formation of the salt LiF (lithium fluoride), which has a strongly negative lattice energy.

Reaction equation 9: reaction of the activated non-ionic state of the ceramic surface with a perfluorinated metal organyl (lithium organyl)

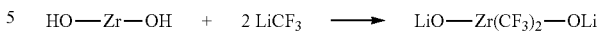

The reaction already described in reaction equation 8 can also be carried out with the non-ionic intermediate state of the activated zirconium oxide surface. A further activation is achieved by the metalation of the surface oxygen, whereby two perfluorinated organyl residues are already attached to the zirconium center. This lithiated surface is able to enter into further nucleophilic reactions.

The reactions outlined above also apply in the same way to other ceramics and high-performance ceramics made from metal oxides.

The aluminum oxide used in a corundum structure is also suitable for these reactions.

Reaction equation 10: Reaction of the aluminum oxide ceramic with hydrofluoric acid

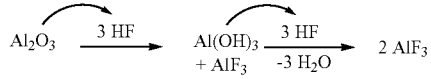

The oxygen in the surface structure of the ceramic is protonated by the hydrofluoric acid, so that Al(OH)₃ and AlF₃ are formed as intermediate stages. Through further protonation of the OH groups, water is split off and the more reactive AlF₃ is formed.

Reaction 11: reaction of the activated ceramic surface with a perfluorinated haloalkyl

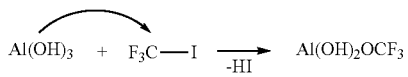

The oxygen in Al(OH)₃ nucleophilically attacks the positively polarized carbon atom of trifluoroiodomethane. Iodine is eliminated as iodide and forms the by-product hydrogen iodide (HI) with the proton of the OH group.

Reaction equation 12: reaction of the activated ceramic surface with a perfluorinated alcohol

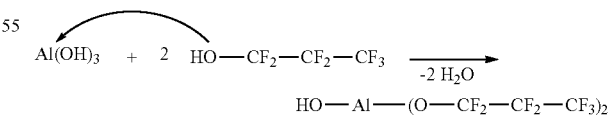

Reaction equation 12: reaction of the activated ceramic surface with a perfluorinated alcohol The alcohol oxygen in the perfluorinated alcohol nucleophilically attacks the aluminum. An OH group is split off as OH⁻ and the alcohol proton (H⁺), which form water as a by-product.

Reaction equation 13: Attachment of a perfluorinated silane to the activated ceramic surface

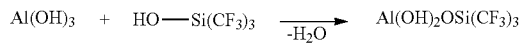

The silane oxygen attacks the aluminum in a nucleophilic manner and the OH and the proton of the silane OH group are split off, so that water is formed as a by-product.

Reaction equation 14: Attachment of a perfluorinated silane to the activated ceramic surface

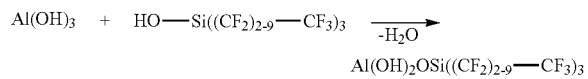

In reaction equation 14, the mechanism proceeds as in equation 13. The silane oxygen attacks the aluminum nucleophilically and OH and the proton of the silane OH group are split off, so that water is formed as a by-product.

Reaction equation 15: reaction of the activated ceramic surface with a perfluorinated lithium organyl

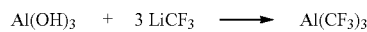

The lithium organyl shown in reaction equation 15 is strongly polarized. The negatively polarized organyl C atom nucleophilically attacks the aluminum. OH— is split off, which forms a by-product with Li+LiOH.

Titanium (IV) oxide ($TiO_2$) is another high-performance ceramic that can be modified by the reactions mentioned above.

Reaction equation 16: Protonation of the oxygen atoms of the $TiO_2$

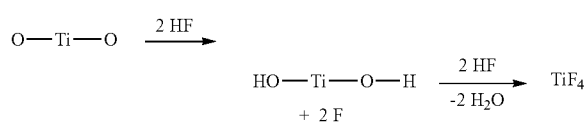

The oxygen atoms on the $TiO_2$ surface are protonated by HF until the more reactive $TiF_4$ is formed.

Reaction equation 17: nucleophilic substitution on the activated ceramic surface

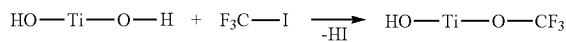

The trifluoroiodomethane shown in reaction equation 17 is polarized, so that an oxygen of the activated ceramic surface attacks the positively polarized carbon atom of the trifluoroiodomethane in a nucleophile manner and iodide is split off. This accumulates with the split off proton to form hydrogen iodide (HI) as a by-product.

Reaction equation 18: activated ceramic surface as electrophile

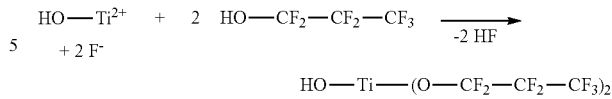

The activated ceramic surface shown in reaction equation 18 reacts as an electrophile and as such is attacked nucleophilically by the oxygen of the perfluorinated alcohol. The proton ($H^+$) of the alcohol group is split off, which combines with a fluoride ion to form HF as a by-product, which is available for further surface activation.

Reaction equation 19: activated ceramic surface as electrophile

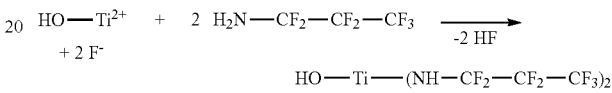

In reaction equation 19, the perfluorinated primary amine acts as a nucleophile. The amine nitrogen attacks the positive titanium in a nucleophilic manner. An $H^+$ of the amino group is split off, which forms the by-product HF with an $F^-$.

Reaction equation 20: Attachment of a perfluorinatd silane to the activated ceramic surface

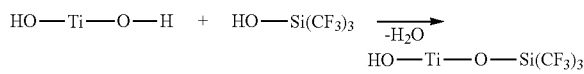

In reaction equation 20, the silane oxygen attacks the titanium on the ceramic surface in a nucleophilic manner. $OH^-$ is split off, which with $H^+$ forms water as a by-product.

Reaction equation 21: Attachment of a perfluorinatd silane to the activated ceramic surface

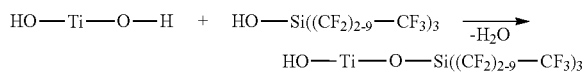

In reaction equation 21, the silane oxygen attacks the titanium of the ceramic surface in a nucleophilic manner. $OH^-$ is split off, which with $H^+$ forms water as a by-product.

Reaction equation 22: addition and hydrogenation of tetrafluoroethene on the activated ceramic surface

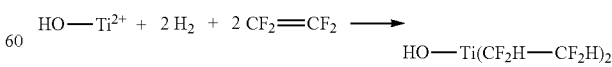

By means of the double bond of the tetrafluoroethene, an addition takes place on the electrophilic titanium. Subsequent hydrogenation (addition of $H_2$) reduces the previous ethene group to a tetrafluoroethane group.

Reaction equation 23: Reaction of a perfluorinated metal organyl with the activated ceramic surface

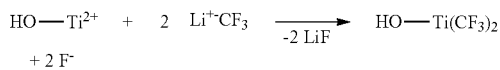

The lithium organyl shown in equation 23 is strongly polarized. The negatively polarized organyl C atom nucleophilically attacks the titanium. OH⁻ is split off, which forms a by-product with Li⁺ LiOH.

Reaction equation 24: reaction of the activated non-ionic state of the ceramic surface with a perfluorinated metal organyl (lithium organyl)

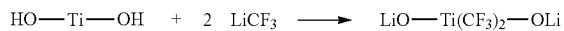

Reaction equation 24 shows, like equation 23, a nucleophilic addition of the negatively polarized organyl to the titanium. In addition, Li⁺ binds to the oxygen atoms on the ceramic surface, so that a still reactive species is created.

Regarding 3) Coating with a Layer on which Functionalized Perfluorinated Compounds can React Instead of activating the ceramic or metal surface for a reaction with the functionalized perfluorinated compounds, a coating with accessible functional groups can alternatively be applied (cf. Examples 1 and 3 of the exemplary inerting routes for plastic surfaces using functionalized perfluorinated compounds)

It can thus be preferred that the ceramic is coated with a polyurethane compound which contains OH groups and bonds well to the surface of the ceramic. A reaction with functionalized perfluorinated compounds can then be brought about via the OH groups, in which case a perfluorinated compound with an isocyanate group is used.

In another example, the ceramic is coated with a polymer compound that contains $NH_2$ groups and bonds well to the surface of the ceramic. A reaction with functionalized perfluorinated compounds is then brought about via the $NH_2$ groups, in which case a perfluorinated compound with an aldehyde group is used.

In a further example, the ceramic is coated with a polymer compound that enables an azide-alkyne cycloaddition. This polymer compound contains azide groups via which the functionalized perfluorinated compounds are bound by means of an alkyne group. Other variants of the click chemistry can also be used.

Exemplary Ways of Inerting Plastic Surfaces Using Functionalized Perfluorinated Compounds:

The inertization of plastic surfaces can be implemented in different ways:

1) Direct chemical connection of the functionalized perfluorinated compounds via functional groups of the plastic
2) Activation of the plastic surface (by plasma, corona or laser treatment, by X-rays or UV radiation, by HF treatment or chemical substances or other processes by which the plastic surface can be activated) and subsequent chemical bonding of the functionalized perfluorinated compounds
3) Coating of the plastic with a layer that is accessible to the chemical attachment of the functionalized perfluorinated compounds with subsequent attachment of these molecules to this layer Through a selective surface treatment (e.g., laser treatment, other) or through a selectively generated print image and the associated accessibility or non-accessibility for the reactions with the functionalized perfluorinated compounds, a defined pattern between areas of different properties (e.g., high and low surface energy or other spatial differentiated properties).

1) Examples for a direct chemical connection of the functionalized perfluorinated compounds to functional groups of plastic surfaces as well as examples for connection to layers that are accessible to the chemical connection of the functionalized perfluorinated compounds:

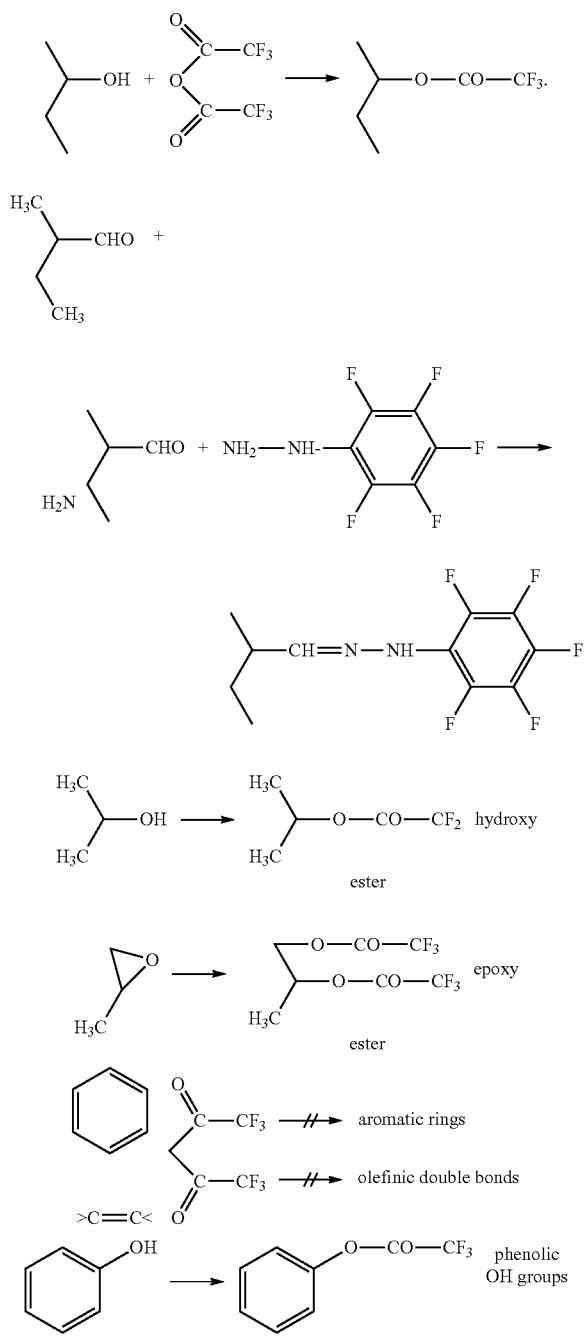

-continued

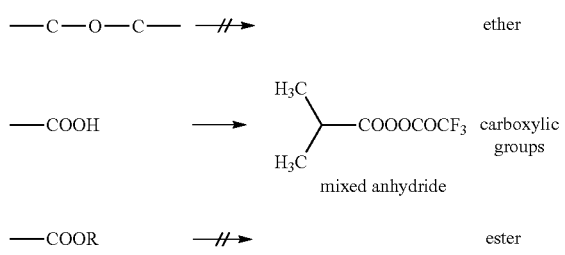

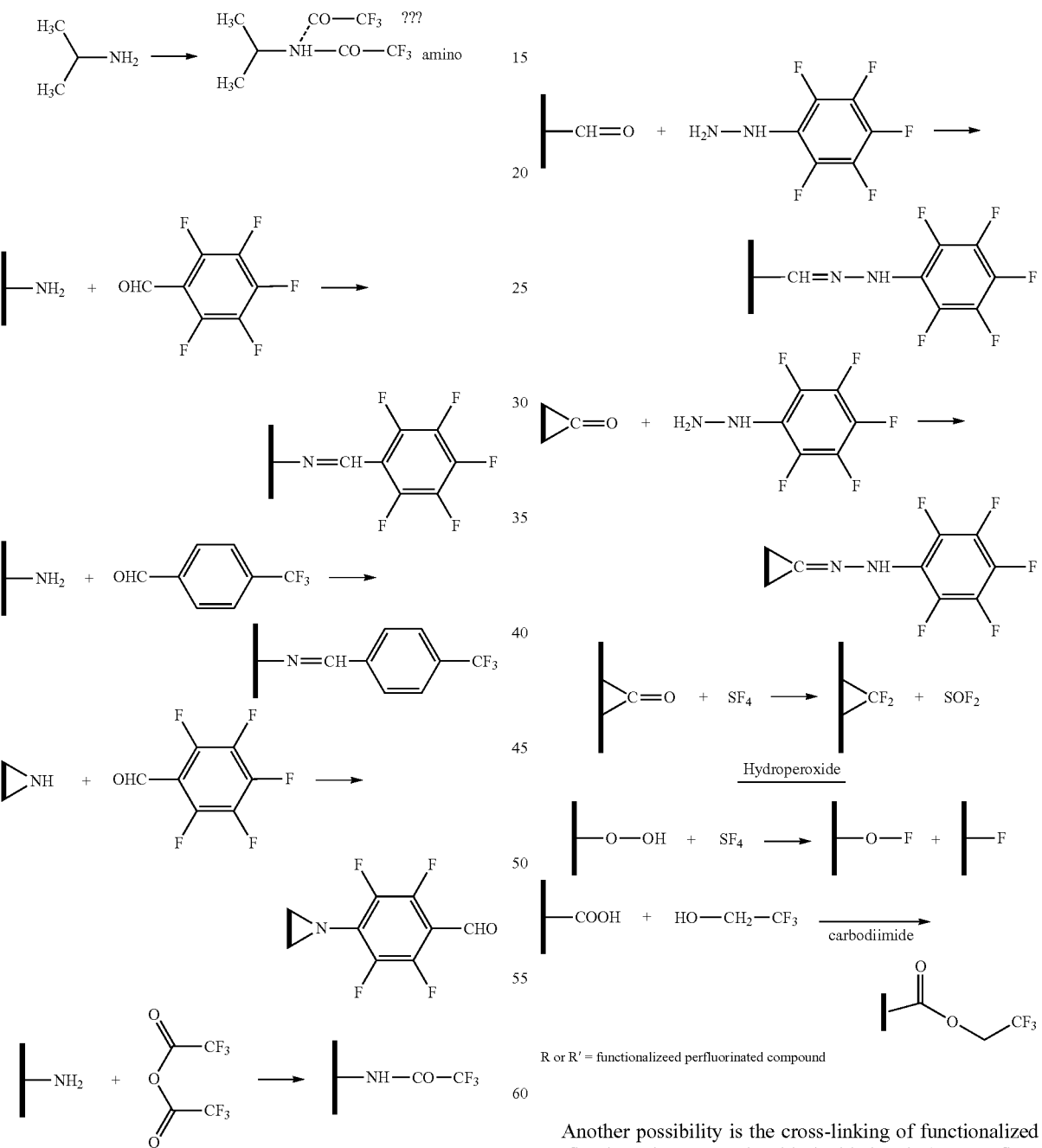

| | TFAA | TFBA, TFMBA | TFE |
|---|---|---|---|
| | | Reagent | |
| Group | Anhydride | Aldehyde | Hydroxyl |
| Primary amine | X | X | |
| Secondary amine | X | (X) | |
| Carboxyl | (X) | | X |
| Hydroxyl | X | | |
| Epoxy | X | | |

R or R' = functionalizeed perfluorinated compound

Examples of possible applications in principle of functionalized perfluorinated compounds on functional groups of a plastic surface or a coating include:

Another possibility is the cross-linking of functionalized perfluorinated compounds with double bonds (e.g., perfluorinated sulfonic acids or perfluorinated carboxylic acids or perfluorinated monomers of plastics such as acrylates) with plastics that also contain double bonds (e.g., polyester) under UVA radiation.

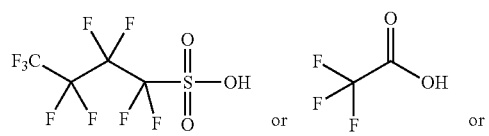

In principle, perfluorinated compounds, whose functional group can be subjected to nucleophilic attack, or positively charged perfluorinated ions are particularly suitable. But other chemical compounds are also possible.

Examples of preferred functionalized perfluorinated compounds:

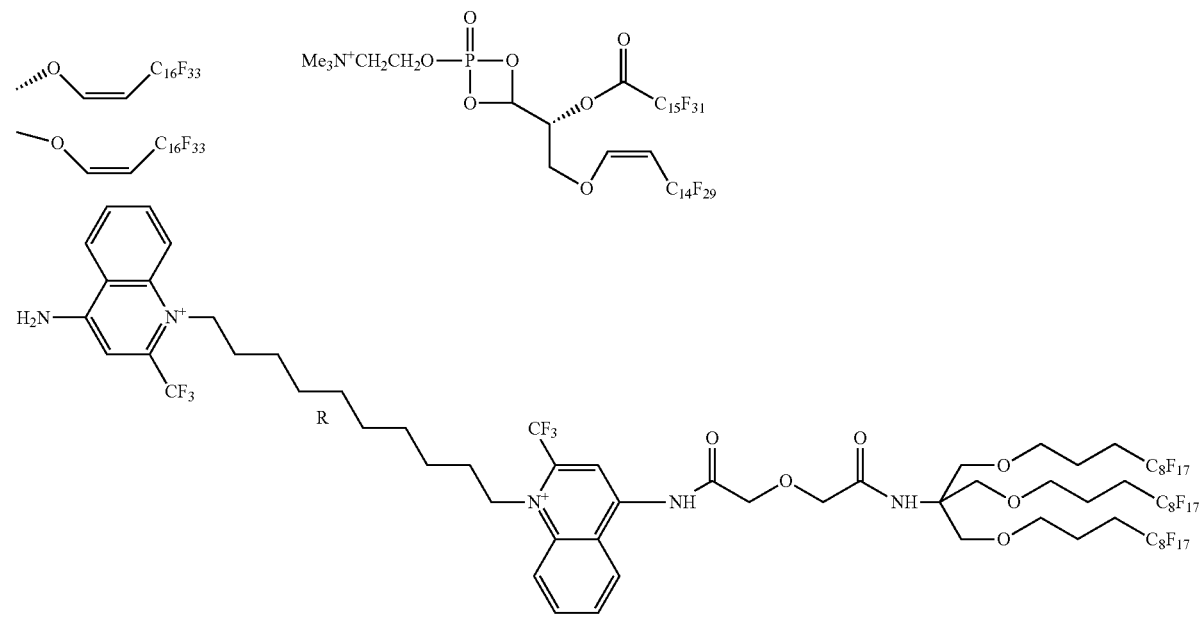

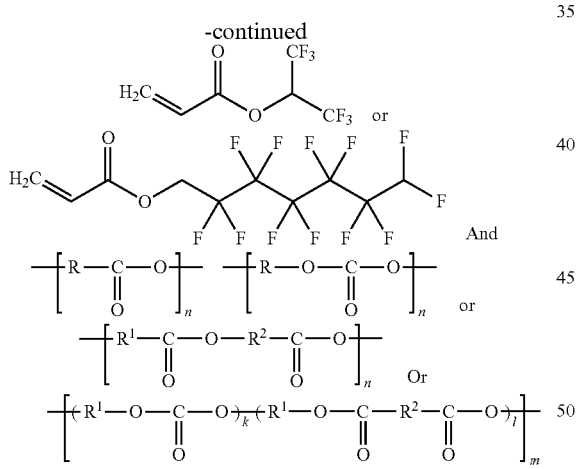

or
or other plastics with a double bond

2) Examples for the activation of the plastic surface (by plasma, corona or laser treatment, by X-rays or UV radiation, by chemical substances or other processes by which the plastic surface can be activated) and subsequent chemical bonding of the functionalized perfluorinated compounds:

In the case of high-energy $O_2$ plasma UV radiation, for example, hydrogen atoms are knocked out of the plastic surface. These are either replaced by oxygen atoms, which are usually present as radicals, or ions are formed. These activated plastic surfaces can then react very well with functionalized perfluorinated compounds.

Without a perfluorinated part of the molecule, the shown molecules would be biodegradable. After attachment to the plastic, the protruding perfluorinated chains shield the attachment from degrading enzymes.

3) Examples of coating the plastic with a layer that is accessible to the chemical attachment of the functionalized perfluorinated compounds with subsequent attachment of these molecules to this layer:

For example, the plastic is coated with a polyurethane compound that contains OH groups. A reaction with functionalized perfluorinated compounds is then brought about via the OH groups, as exemplified above under 1)/3).

In another example, the plastic is coated with a polyacrylamide compound that contains $NH_2$ groups. A reaction with functionalized perfluorinated compounds is then brought about via the NH2 groups, as exemplified above under 1)/3).

In another example, the plastic is coated with a layer that enables an azide-alkyne cycloaddition. This polymer compound contains azide groups via which the functionalized perfluorinated compounds are bound by means of an alkyne group. Other variants of the click chemistry can also be used.

Example Connection of Nonafluoro-1-butanesulfonyl Chloride to Polyurethane:

Polyurethane platelets were wetted with nonafluoro-1-butanesulfonyl chloride (Sigma Aldrich, Art. No. 51974-1G-F) and incubated in a closed container for 30 min at room temperature. The platelets were then washed in isopropanol and with distilled water and dried.

An XPS measurement was carried out to demonstrate the covalent bond (see BAM measurements)

Example Connection of Perfluorobutyryl Chloride to Glass:

An uncoated glass slide was surface-activated in an HF bath for 30 s and then washed in isopropanol and in distilled water and dried.

The glass surface was then wetted with perfluorobutyryl chloride (Sigma Aldrich, Art. No. 257923-5G) and incubated in a closed container for 30 min at room temperature. The glass slide was then washed in isopropanol and dried.

An XPS measurement was carried out to demonstrate the covalent bond (see BAM measurements)

Example Binding of Perfluorobutyryl Chloride to Titanium:

An uncoated titanium support was surface-activated in an HF bath for 30 s and then washed in isopropanol and in distilled water and dried.

The titanium surface was then wetted with perfluorobutyryl chloride (Sigma Aldrich, Art. No. 257923-5G) and incubated in a closed container for 30 min at room temperature. The titanium support was then washed in isopropanol and with distilled water and dried.

An XPS measurement was carried out to demonstrate the covalent bond (see BAM measurements)

Example Binding of Perfluorobutyryl Chloride to Steel:

An uncoated steel support was surface-activated in an HF bath for 30 s and then washed in isopropanol and in distilled water and dried.

The steel surface was then wetted with perfluorobutyryl chloride (Sigma Aldrich, Art. No. 257923-5G) and incubated in a closed container for 30 min at room temperature. The titanium support was then washed in isopropanol and with distilled water and dried. Es erfolgte eine XPS-Messung zum Nachweis der kovalenten Anbindung (siehe BAM-Messungen)

Example Binding of Perfluorobutyryl Chloride to Ceramic:

A ceramic plate was surface-activated in an HF bath for 30 s and then washed in isopropanol and in distilled water and dried.

The ceramic surface was then wetted with perfluorobutyryl chloride (Sigma Aldrich, Art. No. 257923-5G) and incubated in a closed container for 30 min at room temperature. The ceramic plate was then washed in isopropanol and with distilled water and dried.

An XPS measurement was carried out to demonstrate the covalent bond (see BAM measurements)

The invention claimed is:

1. A method for rendering material surfaces inert, comprising:
   a) provision of a material surface, where the material surface is ceramic surface, a metal surface, a glass surface, or a plastic surface;
   b) providing a functionalized perfluorinated compound, where the functionalized a perfluorinated compound comprises a perfluorinated compound and a functional group, the functionalized perfluorinated compound is selected from the group consisting of $C_2F_5I$, $C_3F_7Br$, $C_4F_9I$, $C_5F_{11}Br$, $C_6F_{13}Br$, $C_8F_{15}Br$, $C_4F_9CH=CHC_4F_9$, $C_8F_{16}C_{12}$, $C_{10}F_{19}N$, $C_6F_{19}Br$, $C_9F_{21}N$, $C_{10}F_{21}Br$, $C_{11}F_{22}N_2O_2$, $C_6F_{13}CH=CHC_6F_{13}$, $C_{12}F_{27}N$, $C_{16}F_{25}Br$, $C_8F_{17}I$ and $C_8F_{17}Br$;
   c) direct reaction of the functionalized perfluorinated compound with the surface to form a covalent bond, an ionic relationship or a metal bond between the perfluorinated compound and the material surface, wherein the surface is pre-activated prior to the step c); and
   wherein the pre-activation takes place by acid, laser, corona, or ozone treatment, wherein different activation takes place for partial areas of the material surface.

2. The method according to claim 1, wherein
   the functionalized perfluorinated compound is a perfluorinated compound with at least one functional group that comprises at least one double bond and can be attached to the surface by forming a covalent bond to the surface by UV cross-linking.

3. The method according to claim 1, wherein
   the material surface is:
   the ceramic surface which is formed of a ceramic selected from a group consisting of: aluminum oxide, zirconium oxide, aluminum titanate, silicon carbide, silicon nitride, aluminum nitride or other non-metallic or metallic substances or dispersion ceramics and piezoceramics, porcelain, stoneware, stealite, glass ceramic, cordlerite, titanium oxide, yttrium oxide, beryllium oxide, magnesium oxide, uranium oxide, titanate, lead titanium zirconate, ferrites, carbon, nitrides, carbides, borides, and silicides (silicon, boron, titanium, molybdenum),
   the metal surface which is formed by a metal selected from a group consisting of: titanium, aluminum, cadmium, chromium, iron, gold, iridium, cobalt, copper, nickel, palladium, platinum, silver, zinc and tin and alloys which contain any of these, or
   the plastic surface which is formed by a plastic selected from a group consisting of: polyacetals, polyacrylates, polyamides, polyaryls, celluloses, polyesters, polyoleofins, polystyrenes, polyvinyacates, polyvinylchlorides, polyetherketones, polyaryletherketones, polylactides, amino resins, epoxy resins, polyether alcohols, butadiene elastomers, fluorocarbon elastomers, ester elastomers, isoprene elastomers, olefin elastomers, silicone elastomers, pentenes elastomers, sulfide elastomers, urethane elastomers and vinyl chloride elastomers.

4. The method according to claim 1, wherein the functionalized perfluorinated compound is a perfluorinated compound with at least one functional group that can be attached to radicals or protons.

5. The method according to claim 1, wherein the activation takes place by laser, corona, or ozone treatment.

6. The method according to claim 1, wherein different activation takes place for partial areas of the material surface by laser treatment.

* * * * *